(12) United States Patent
Polley et al.

(10) Patent No.: US 9,810,759 B2
(45) Date of Patent: Nov. 7, 2017

(54) CLOSED-LOOP DEVICE CALIBRATION USING A WIDEBAND SIGNAL

(71) Applicant: Texas Instruments Incorporated, Dallas, TX (US)

(72) Inventors: Arup Polley, Richardson, TX (US); Russell Melvin Rosenquist, Plano, TX (US); Terry Lee Sculley, Lewisville, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 29 days.

(21) Appl. No.: 14/995,521

(22) Filed: Jan. 14, 2016

(65) Prior Publication Data

US 2017/0192078 A1    Jul. 6, 2017

Related U.S. Application Data

(60) Provisional application No. 62/273,033, filed on Dec. 30, 2015.

(51) Int. Cl.
*G01R 35/00* (2006.01)
*G01R 33/07* (2006.01)
(Continued)

(52) U.S. Cl.
CPC ........... *G01R 35/005* (2013.01); *G01R 33/07* (2013.01); *G01N 1/00* (2013.01); *G01N 2201/00* (2013.01); *H04J 1/00* (2013.01)

(58) Field of Classification Search
CPC ........ G01N 1/00; G01N 2201/00; G01C 1/00; H04J 1/00; H04J 2203/00; H03C 1/00; H03C 2200/00
See application file for complete search history.

(56) References Cited

U.S. PATENT DOCUMENTS 5,640,385 A * 6/1997 Long .................... H04B 7/2631
                                                        370/335
5,706,275 A * 1/1998 Zhengdi ................ H04B 1/707
                                                        370/204

(Continued)

OTHER PUBLICATIONS

Allegro Microsystems, LLC; "Fully Integrated, Hall Effect-Based Linear Currently Sensor IC with 2.1 kVRMS Isolation and a Low-Resistance Current Conductor" product information sheet; copyright 2006-2013; Worchester, MA; 15 pages.

(Continued)

*Primary Examiner* — Jermele M Hollington
*Assistant Examiner* — Temilade Rhodes-Vivour
(74) *Attorney, Agent, or Firm* — John R. Pessetto; Charles A. Brill; Frank D. Cimino

(57) ABSTRACT

A closed-loop calibration scheme is configured to allow a device to remain in continuous operation. A signal generator device provides a pseudorandom sequence for a signal received by a magnetic field magnetic field sensor, such as a Hall-effect sensor. A signal decoder circuit receives the output signal and decouples the generated spread spectrum signal from the interference by measuring the gain in the overall signal. The decoder device distinguishes the known spread spectrum signal from any perturbation effects of particular bandwidths. A processing circuit then outputs a signal that has an operation parameter that has been adjusted to compensate for the perturbation effects. The processing circuit provides the receiver circuit with the compensation signal, hence forming a closed-loop calibration configuration.

14 Claims, 4 Drawing Sheets

(51) Int. Cl.
*G01N 1/00* (2006.01)
*H04J 1/00* (2006.01)

(56) References Cited

U.S. PATENT DOCUMENTS

| | | | |
|---|---|---|---|
| 9,300,354 B2* | 3/2016 | Floch | G01C 21/20 |
| 2004/0223573 A1* | 11/2004 | Brown | H04L 27/2017 |
| | | | 375/375 |
| 2010/0103982 A1* | 4/2010 | Smith | G01C 21/165 |
| | | | 375/135 |
| 2011/0298506 A1* | 12/2011 | Salle | G01S 7/032 |
| | | | 327/156 |

OTHER PUBLICATIONS

Infineon Technologies AG; "TLI4970-D050T4 High precision miniature coreless magnetic current sensor for AC and DC measurements with digital interface and fast overcurrent detection" Data Sheet; Rev. 1.0, Nov. 21, 2014; Sense & Control product description; 29 pages.

Simon, P.L.C. et al.; "Autocalibration of Silicon Hall Devices"; Sensors and Actuators A 52 (1996), 203-207; Elsevier Science S.A.; 5 pages.

Pastre, M., et al.; "A Hall Sensor Analog Front End for Current Measurement with Continuous Gain Calibration"; IEEE Sensors Journal, vol. 7, No. 5, May, 2007; 8 pages.

* cited by examiner

CLOSED-LOOP DEVICE CALIBRATION USING A WIDEBAND SIGNAL

RELATED APPLICATION(S)

This application claims the benefit of U.S. provisional patent application number 62/273,033 filed Dec. 30, 2015, the contents of which are incorporated by reference as if fully rewritten herein.

TECHNICAL FIELD

This invention relates generally to calibration of devices and, in particular, to using application of a signal to a device to derive feedback information for the device's operation such as closed-loop calibration of a Hall-effect sensor.

BACKGROUND

Open and closed loop calibration methods are generally known and applied in a variety of contexts. One such context is in the calibration of Hall-effect magnetic field sensors. Hall-effect magnetic field sensors are solid state magnetic sensor devices that can be used to measure magnetic fields. Applications of Hall-effect magnetic field sensors require high accuracy; however, they are known to suffer from variation and drift in sensitivity with process variations, temperature, and package stress changes. The conventional solution to control for the complex temperature dependence that Hall-effect sensors exhibit is to implement so-called "open-loop" temperature compensation circuitry configurations. Fine-tuning (or "trimming") the sensitivity of each part for the process variation may be carried out, and the changes in sensitivity with temperature and stress may be compensated for by using on-chip temperature and stress sensors and pre-evaluated compensation tables. This approach requires expensive multi-point characterization of individual devices and re-calibration over time. The magnetic field excitation for calibration of the sensor can be created using an on-chip current coil or external magnetic field sources. Calibration, however, can only be performed when the device is offline and hence, not in operation, as the signal to be measured can interfere with the calibration signal.

As an alternative to the open-loop scheme, closed-loop methods have been implemented to perform continuous calibration in the absence of external magnetic fields. Closed-loop calibration typically works as follows: a known magnetic field is applied to the device (a method of generating known magnetic field would be: a known temperature-insensitive current is passed through an on-chip/off-chip coil/other suitable trace near the sensor), the sensor output is then compared with the desired response, and the sensor sensitivity/gain is adjusted to minimize the comparator error. This results in much higher accuracy than the open-loop configuration.

A known issue with conventional closed-loop calibration of a Hall-effect sensor is that the calibration current near the Hall-effect sensor can generate enough heat that it changes the operating temperature, resulting in a change of sensitivity and affecting the primary measurement. Additionally, closed-loop calibrations have been demonstrated to perform well in the absence of external magnetic fields, but completely eliminating interference in real-world applications is non-trivial and can require offline calibration in a magnetically shielded environment.

SUMMARY

Generally speaking, pursuant to these various embodiments, a closed-loop calibration scheme may be configured in such a manner for a device to remain in continuous operation (i.e., online). In one particular example, a signal generator device is configured to provide a pseudorandom sequence spreading the signal over a wide range of frequencies. This "spread spectrum" signal is received by a magnetic field generator, which provides an encoded or "spread spectrum" magnetic field signal to a magnetic field sensor, such as a Hall-effect sensor. External interference of particular bandwidths can influence the overall sensor output signal. A signal decoder circuit receives the output signal, however, and can decouple the generated spread spectrum signal from the interference by using an appropriate decoding scheme on the overall received signal. By definition, the spread spectrum signal is spread over the frequency domain, so the decoder device acts to distinguish the known spread spectrum signal from any interference of particular bandwidths. The output corresponding to the spread spectrum signal, however, is dependent on any perturbation effect that changes the sensitivity of the magnetic sensor. A processing circuit can then output a signal that has an operation parameter that can be adjusted to compensate for said perturbation effects. The processing circuit provides the receiver circuit with the compensation signal, hence forming a closed-loop calibration configuration.

This scheme enables the use of a small calibration signal (current) avoiding the previously presented problem of heat generation near the Hall-effect sensor, thereby maintaining the operating temperature. Such a configuration allows for continuous calibration, eliminating the need for expensive multi-point temperature testing. Furthermore, the device is thus able to continually remain in operation These and other benefits may become clearer upon making a thorough review and study of the following detailed description.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Figure 1:
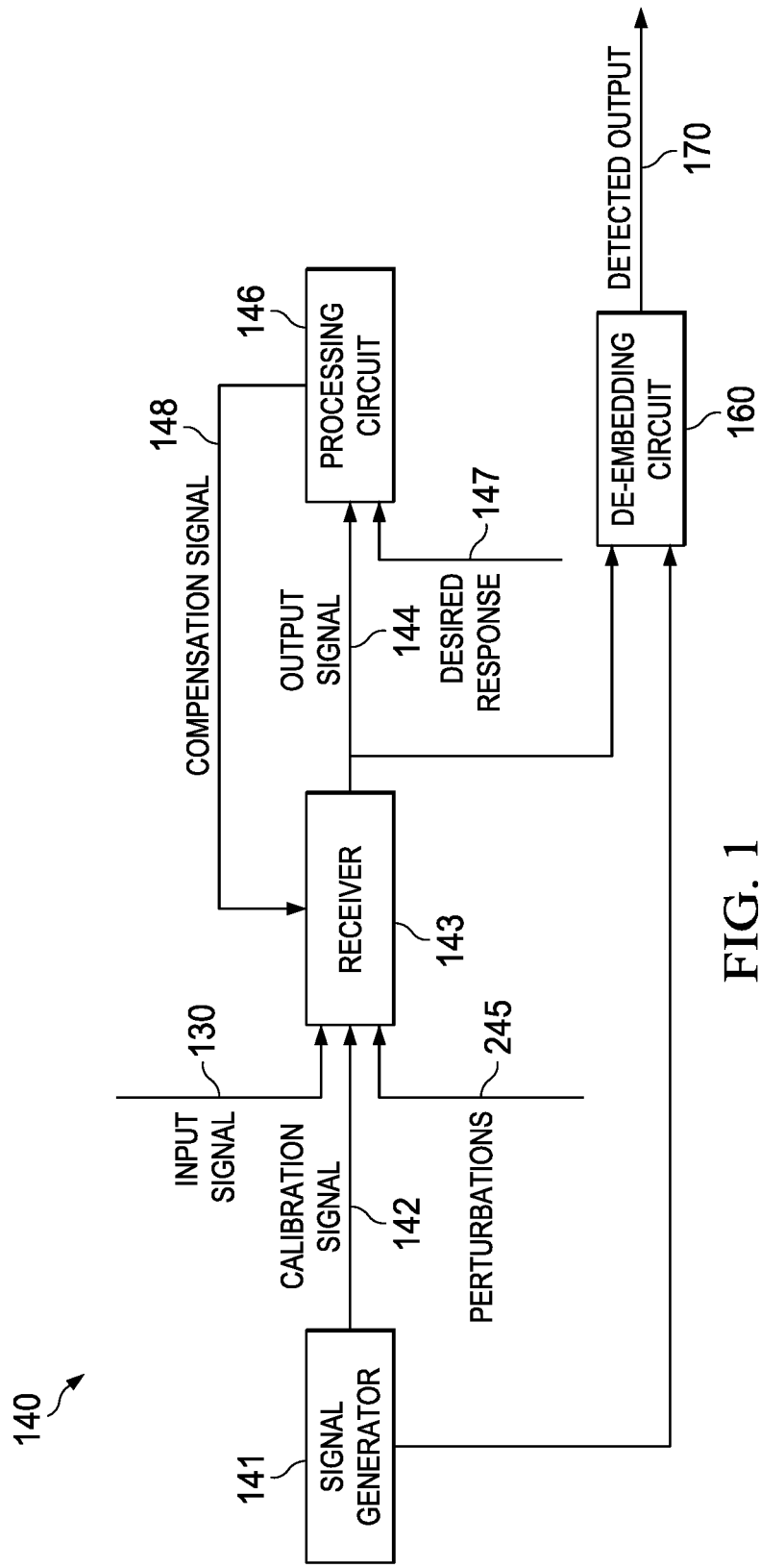
FIG. 1 is a block diagram of an example device with a closed-loop calibration configuration in accordance with various embodiments of the invention.

Referring now to the drawings, and in particular to FIG. 1, a simplified closed-loop calibration circuitry device example 140 is shown. In this configuration, a signal generator device 141 provides a pseudorandom wideband calibration signal 142, wherein a nearly random sequence of bits (e.g., ones and zeros) is spread over a wide range of frequencies. A receiver circuit device 143 then receives the calibration signal 142 and outputs a new signal 144 that is at least dependent on said wideband calibration signal 142, any input signal 130 that the device is supposed to measure, as well as other possible perturbation effects 145 that changes the response/characteristics of the receiver 143 such as temperature effects. A processing circuit 146 receives the output signal 144 and a desired response signal 147. In this manner, the processing circuit 146 may determine what compensation signal 148 should then be applied back to the receiver circuit device 143. The compensation signal 148 effects adjustment of an operation parameter thereby countering said perturbation effects 145 based on a comparison of at least an aspect of the output 144 based on the pseudorandom wideband calibration signal 142 and the desired response signal 147. The receiver circuit device 143 receives said compensation signal 142, thereby forming a closed-loop calibration configuration, and the device 140 can remain in continuous operation. Separately, a de-embedding circuit 160 provides a detected output 170 that includes only the aspects of the input signal 130 while removing the effects of the pseudorandom wideband calibration signal.

Generally speaking, the receiver circuit device 143 can be any device that receives outside signals and provides an output that is dependent on the received outside signals. Examples include magnetic field detectors such as a Hall-effect sensor, magneto-resistive sensor (XMR) like anisotropic magneto-resistive (AMR), giant magneto-resistive (GMR), tunneling magneto-resistive (TMR), colossal magneto-resistive (CMR), fluxgate sensor etc. The approaches described herein are further applicable to other types of sensors such as infrared sensors, photosensors, audio sensors, ultrasound sensors, and the like. In the example where the receiver circuit device 143 is a magnetic field detector, the de-embedding circuit 160 effectively separates out from the output signal 144 aspects due to the calibration signal 142 such that the de-embedding circuit 160 can then provide a detected output that accurately depicts the otherwise sensed magnetic field.

Figure 2:
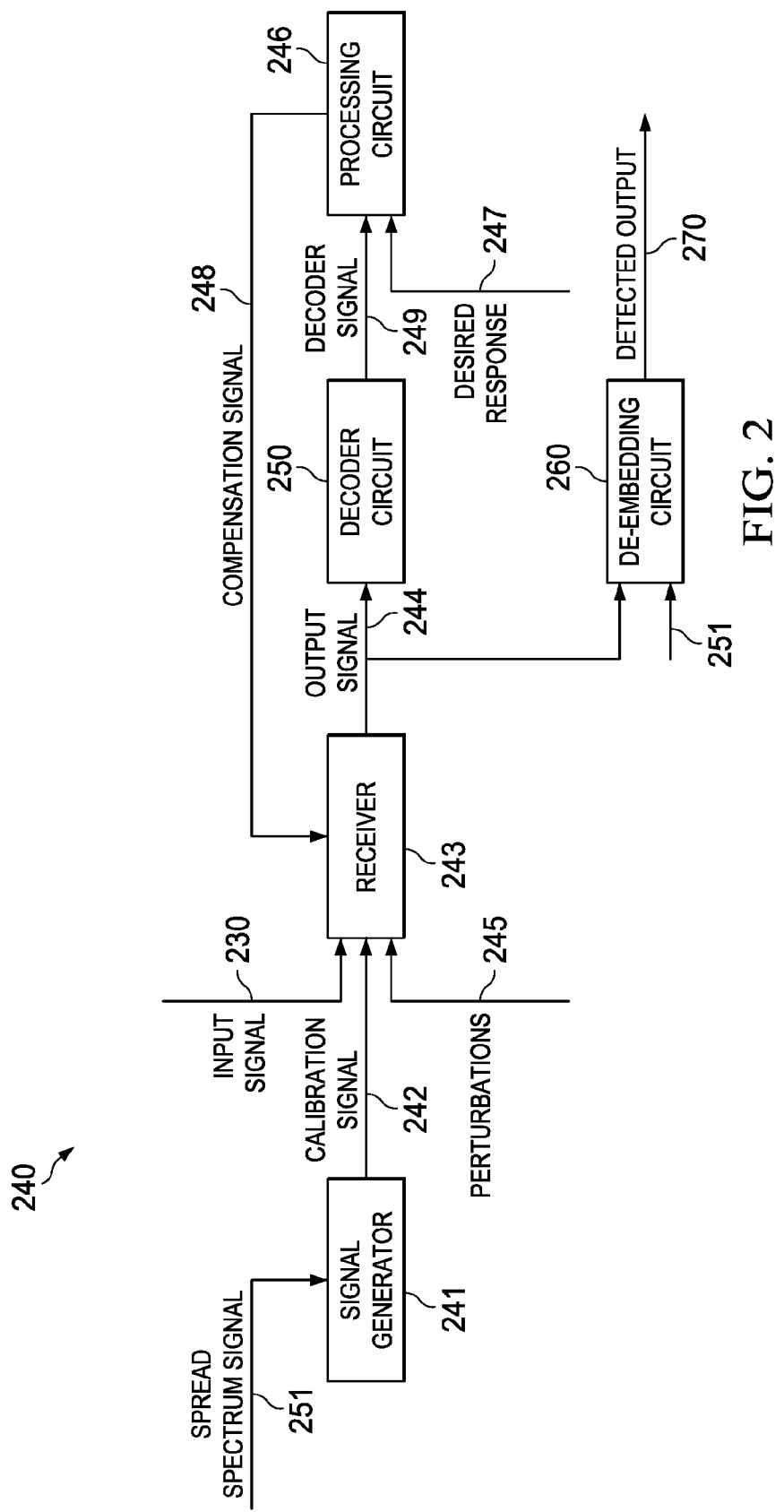
FIG. 2 is a block diagram of another example device with a closed-loop calibration further configured to consist of a spread spectrum signal and decoder circuit in accordance with various embodiments of the invention.

In another approach illustrated in FIG. 2, the device is configured in such a manner that the signal generator 241 is further comprised of a spread spectrum signal. The spread spectrum technique takes a generated signal of a particular bandwidth (the pseudorandom wideband calibration signal 242 in this embodiment) and expands it in the frequency domain. The encoded spread spectrum signal is known to resist interference and hence may remain distinguishable from any perturbation effects 245.

A receiver circuit 243 is configured to receive the pseudorandom wideband calibration signal 242, which now comprises a spread spectrum signal 251. A (spread spectrum) decoder circuit 250 then receives the output signal 244 from the receiver circuit 243 that is comprised of the pseudorandom wideband calibration signal 242 as well as any input signal 230 sensed by the receiver circuit 243. The response or transfer function of the receiver is also affected by any additional perturbation 245. The decoder circuit 250 detects the spread spectrum signal and, in turn, separates the known pseudorandom wideband calibration signal 242 from the input signal 230. This decoded signal 249 is sent to the processing circuit 246 that may then compare the decoded signal 249 to the desired response signal 247. A compensation signal 248 may now be sent from the processing circuit 246 back to the receiver circuit 243, thus forming a closed-loop configuration, and allowing for an highly accurate, iterative process. Separately, the de-embedding circuit 260 provides a detected output 270 that includes aspects of the output not based on the pseudorandom wideband calibration signal, but only based on the input signal 230 detected by the receiver circuit 243.

Figure 3:
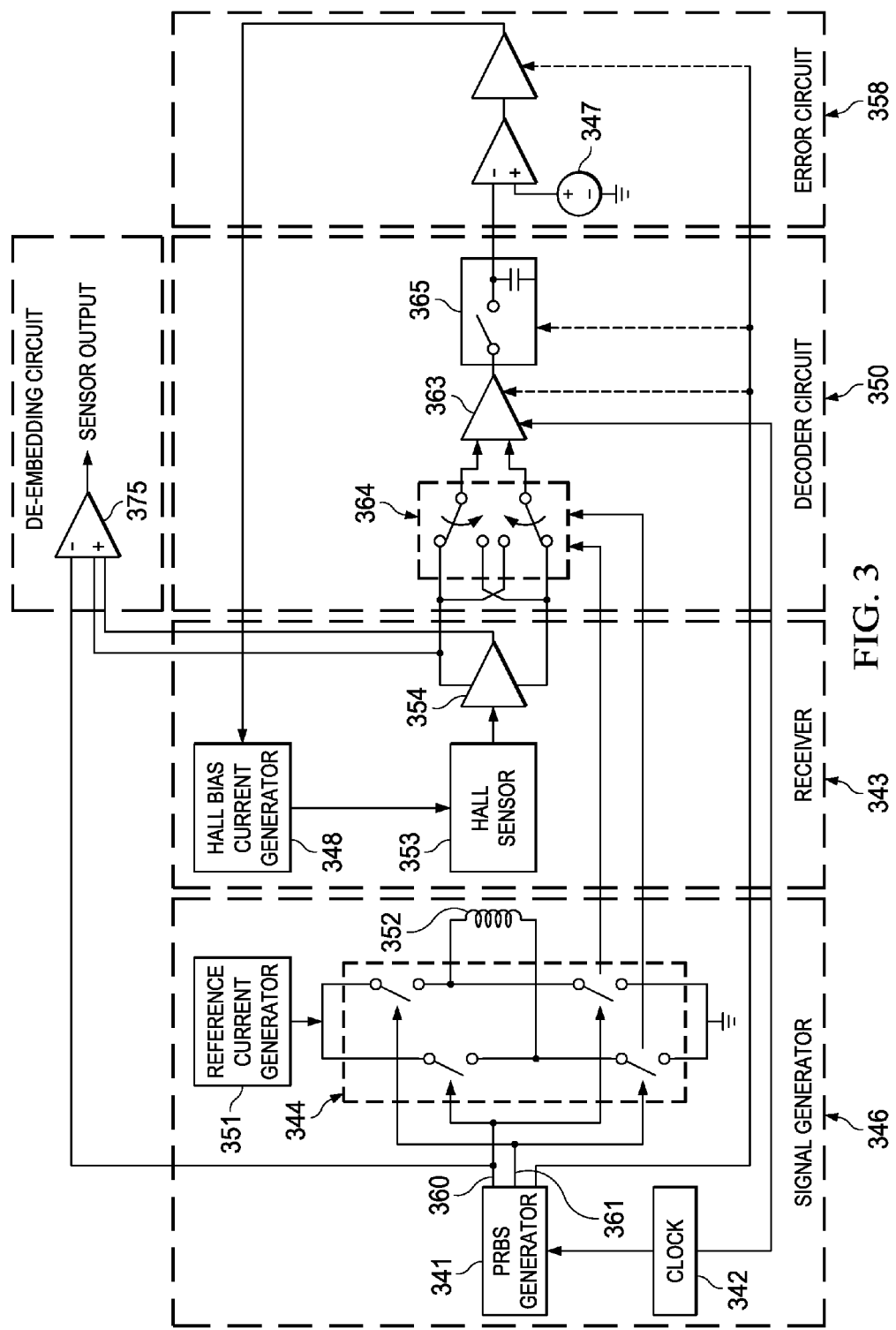
FIG. 3 is circuit diagram of an example device similar to FIG. 2, further including a Hall-effect sensor and additional circuitry elements in accordance with various embodiments of the invention.

FIG. 3 illustrates another example of a closed-loop calibration apparatus. In this configuration, the signal generator circuit is a pseudorandom bit sequence ("PRBS") signal generator 341. The PRBS generator 341 provides a signal to generate a magnetic field of known frequency to be supplied to the receiver circuit device that, in this example, is a magnetic field detector 343. A reference current generator 351 provides current to a coil 352 to create the calibration magnetic field for the magnetic field detector 343 such that it receives the magnetic field that changes with the pseudorandom wideband calibration signal. The H-bridge-like switch combination 344 is the modulator that changes the direction of current through the coil 352 depending on the PRBS electrical signal to facilitate provision of a PRBS magnetic signal. The PRBS magnetic field signal is received by a Hall-effect sensor 353, which may be a nearby the coil 352. A Hall-effect sensor frontend circuit 354 receives the generated magnetic field current from the Hall-effect sensor 353 and interfaces with the decoder circuit 350.

Generally speaking, the decoder circuit 350 allows for discrete time signal processing of the output from the sensor. In this example, the decoder circuit 350 receives the output from the Hall-effect sensor frontend circuit 354 and the pseudorandom wideband calibration signal and provides the aspect of the output based on the pseudorandom wideband calibration signal for comparison to the desired device response signal. As illustrated in FIG. 3, this circuit includes the switched capacitor demodulator 364, SC integrator circuit 363, and a sample and hold circuit 365. The SC demodulator 364 is configured to receive the output from the receiver circuit device 343 and the pseudo random bit sequence generated by the PRBS generator 341 and generates a demodulated signal. The SC integrator 363 receives the demodulated signal and a clock signal provided by a clock 342 for the pseudorandom wideband calibration signal to create an integrated signal. The SC integrator circuit 363 derives the aspect of the output based on the pseudorandom wideband calibration signal and integrates the aspect of the output based on the pseudorandom wideband calibration signal over a time period to provide an integrated output. The integrated output is stored in the sample and hold circuit 365 for the entire length of the PRBS sequence until the next integrated signal. The stored signal is used for comparison to the desired device response signal.

More specifically, in this example of FIG. 3, a differential signaling is used. The PRBS signal S 360 and its inverse Sbar 361 are used as a modulating signal for the PRBS modulator 344. The output from the receiver circuit device 343 is also a differential signal, which is demodulated using the PRBS signal S and Sbar.

The processing circuit 346 further includes an error circuit 358. The error circuit 358 includes an error amplifier 357 configured to receive the desired device response signal 347 and the integrated output from the sample and hold circuit 365. The error amplifier 357 outputs an error signal through comparison between the received signals. A loop stabilizing switched capacitor integrator circuit 359 is configured to receive the error signal and to provide the compensation signal based on the error signal. The compensation signal is routed as feedback to the Hall bias current generator 348 to help control the Hall effect sensor 353.

The processing circuit 346 also includes a calibration signal cancellation/de-embedding circuit 375 configured to receive the output from the Hall-effect sensor frontend circuit 354 and the pseudorandom wideband calibration signal. The calibration signal cancellation circuit 375 provides a clean output signal removing effects of application of the pseudorandom wideband calibration signal to the Hall Effect sensor 353.

Figure 4:
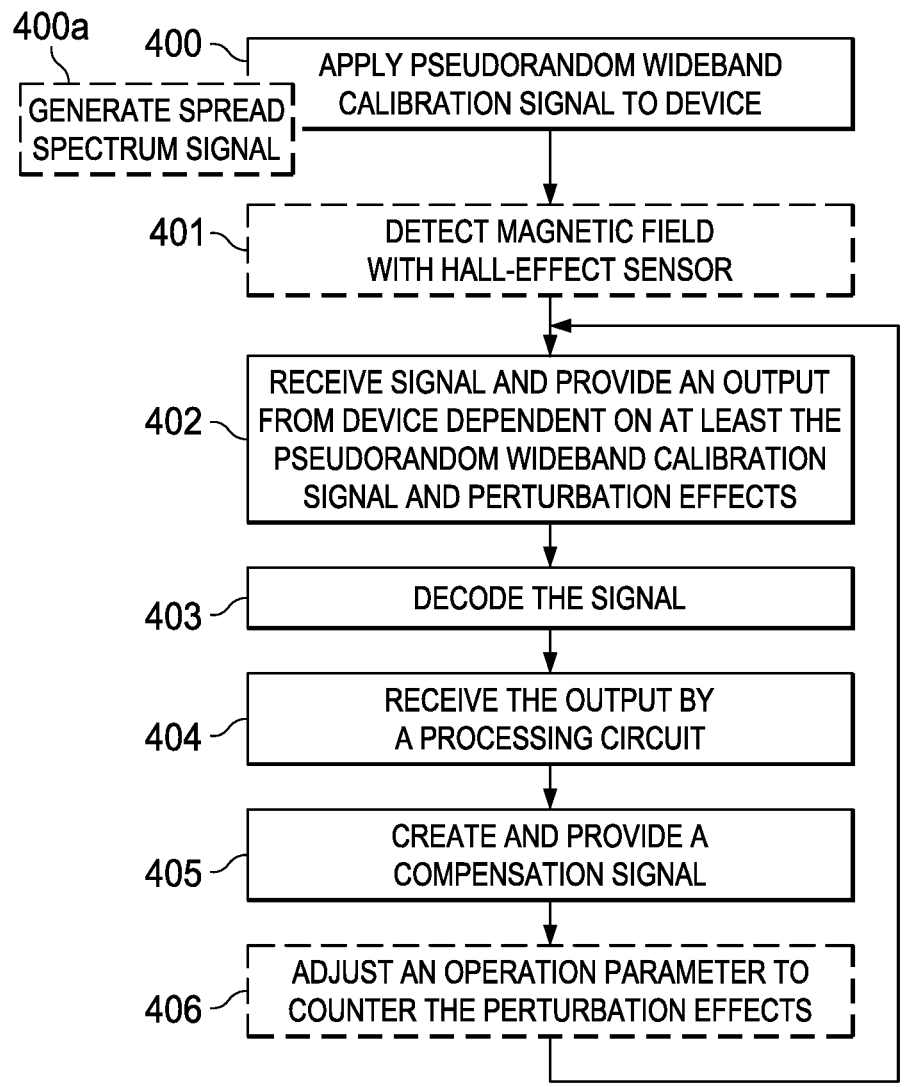
FIG. 4 is a flow chart illustrating a method of operation in accordance with various embodiments of the invention.

An example method of operation in accord with these disclosures is illustrated in FIG. 4. The method includes applying a pseudorandom wideband calibration signal generated by a signal generator to a receiving device 400; an example of a generated pseudorandom wideband calibration signal is a spread spectrum signal 400*a*. This application can be effected using an integrated or nearby coil disposed with the device, for example, in the case where the device is a Hall-effect sensor, which detects 401 the applied magnetic field that changes with the pseudorandom wideband calibration signal together with other magnetic fields that engage the device. Accordingly, the receiver device provides 402 an output dependent on at least the pseudorandom wideband calibration signal and perturbation effects as well as the other sensed signals (e.g., magnetic fields).

The output signal is then decoded 403 by a decoder circuit that disentangles the known pseudorandom wideband calibration signal from the other sensed signals but while retaining the effect of the external perturbations. The decoded signal is received 404 by a processing circuit and compared to a desired device response signal to create 405 a compensation signal.

The creation and provision 405 of the compensation signal can be performed in any number of ways including those described above. By one approach, this step can be performed by receiving the output and the pseudorandom wideband calibration signal by a decoder circuit and providing by the decoder circuit the aspect of the output based on the pseudorandom wideband calibration signal for comparison to the desired device response signal.

In one particular implementation of the method, for instance as performed by the circuit of FIG. 3, a demodulator circuit receives the output and the pseudorandom wideband calibration signal. The aspect of the output based on the pseudorandom wideband calibration signal is derived and integrated over a time period to provide an integrated output. The integrated output is provided to a sample and hold circuit configured to receive and store for comparison to the desired device response signal. An error amplifier receives the desired device response signal in an error amplifier and the integrated output from the sample and hold circuit. The error amplifier outputs an error signal received by a loop stabilizing switched capacitor integrator circuit, which in turn provides the compensation signal based on the error signal. The compensation signal is used to adjust 406 an operation parameter to counter the perturbation effects for the device based on a comparison of an aspect of the output based on the pseudorandom wideband calibration signal and the desired device response signal. Now the configuration of the device can form a closed loop as the receiver circuit is provided with signal that compensates for the perturbation effects.

So configured, the closed loop approach allows for fine-tuning of the sensor device without having to remove outside influences from the sensor. In the Hall-Effect example, there is no need to shield the Hall-Effect sensor from outside magnetic fields to adjust its parameters. Similarly, perturbation effects based on temperature or on-chip environmental factors can be addressed on the fly.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus comprising:
   a signal generator device configured to provide a pseudorandom wideband calibration signal;
   a device configured to receive the calibration signal and to provide an output dependent on at least the pseudorandom wideband calibration signal and perturbation effects;
   a processing circuit configured to receive the output and a desired device response signal and to provide a compensation signal configured to adjust an operation parameter to counter the perturbation effects for the device based on a comparison of an aspect of the output based on the pseudorandom wideband calibration signal and the desired device response signal;
   the device further comprises a magnetic field detector; and
   the signal generator device is configured to provide the pseudorandom wideband calibration signal to cause a magnetic field applied to the magnetic field detector to change with the pseudorandom wideband calibration signal.

2. The apparatus of claim 1 wherein the processing circuit is further configured to provide a detected output comprising aspects of the output not based on the pseudorandom wideband calibration signal.

3. The apparatus of claim 1 wherein the magnetic field detector comprises a Hall Effect sensor; and the apparatus further comprises an integrated or nearby coil disposed with the Hall Effect sensor to provide the magnetic field that changes with the pseudorandom wideband calibrations signal to the Hall Effect sensor.

4. The apparatus of claim 3 wherein the processing circuit further comprises:
   a calibration signal cancellation circuit configured to receive the output and the pseudorandom wideband calibration signal and provide a clean output signal removing effects of application of the pseudorandom wideband calibration signal to the Hall Effect sensor;
   a decoder circuit configured to receive the output and the pseudorandom wideband calibration signal and provide the aspect of the output based on the pseudorandom wideband calibration signal for comparison to the desired device response signal.

5. The apparatus of claim 4 wherein:
the decoder circuit further comprises:
- a switched capacitor integrator circuit configured to receive the output and a clock signal for the pseudorandom wideband calibration signal, to derive the aspect of the output based on the pseudorandom wideband calibration signal, and to integrate the aspect of the output based on the pseudorandom wideband calibration signal over a time period to provide an integrated output;
- a sample and hold circuit configured to receive and store the integrated output for the time period and provide the integrated output for comparison to the desired device response signal;

the processing circuit further comprising:
- an error amplifier configured to:
    receive:
      the desired device response signal, and
      the integrated output from the sample and hold circuit; and
    output an error signal;
- a loop stabilizing switched capacitor integrator circuit configured to receive the error signal and to provide the compensation signal based on the error signal.

6. A method comprising:
applying a pseudorandom wideband calibration signal to a device;
providing an output from the device dependent on at least the pseudorandom wideband calibration signal and perturbation effects;
receiving the output by a processing circuit;
providing by the processing circuit a compensation signal;
using the compensation signal to adjust an operation parameter to counter the perturbation effects for the device based on a comparison of an aspect of the output based on the pseudorandom wideband calibration signal and the desired device response signal;
further comprising detecting with the device a magnetic field; and applying an applied magnetic field to the device that changes with the pseudorandom wideband calibrations signal.

7. The method of claim 6 further comprising providing by the processing circuit a detected output comprising aspects of the output not based on the pseudorandom wideband calibration signal.

8. The method of claim 6 wherein detecting the magnetic field comprises detecting the magnetic field with a Hall Effect sensor; and the method further comprising providing the applied magnetic field that changes with the pseudorandom wideband calibration signal to the Hall Effect sensor by an integrated or nearby coil disposed with the Hall Effect sensor providing the magnetic field that changes with the pseudorandom wideband calibrations signal to the Hall Effect sensor.

9. The method of claim 8 wherein the providing by the processing circuit the compensation signal further comprises:
receiving by a calibration signal cancellation circuit the output and the pseudorandom wideband calibration signal;
providing by the calibration signal cancellation circuit a clean output signal removing effects of application of the pseudorandom wideband calibration signal to the Hall Effect sensor;
receiving the output and the pseudorandom wideband calibration signal by a decoder circuit; and
providing by the decoder circuit the aspect of the output based on the pseudorandom wideband calibration signal for comparison to the desired device response signal.

10. The method of claims 9 wherein the providing by the processing circuit the compensation signal further comprises:
receiving by a switched capacitor integrator circuit the output and a clock signal for the pseudorandom wideband calibration signal;
deriving the aspect of the output based on the pseudorandom wideband calibration signal;
integrating the aspect of the output based on the pseudorandom wideband calibration signal over a time period to provide an integrated output; and
providing the integrated output to a sample and hold circuit configured to receive and store for comparison to the desired device response signal.

11. The method of claims 10 wherein the providing by the processing circuit the compensation signal further comprises:
receiving in an error amplifier the desired device response signal and the integrated output from the sample and hold circuit;
outputting an error signal;
receiving by a loop stabilizing switched capacitor integrator circuit the error signal;
providing from the loop stabilizing switched capacitor integrator circuit the compensation signal based on the error signal.

12. An apparatus comprising:
a Hall Effect sensor;
a signal generator device configured to provide a pseudorandom wideband calibration signal to modulate a magnetic field applied to the Hall Effect sensor;
wherein the Hall Effect sensor is configured to provide an output dependent on at least the pseudorandom wideband calibration signal and perturbation effects;
a processing circuit configured to:
    receive the output and a desired device response signal,
    provide a compensation signal configured to adjust an operation parameter to counter the perturbation effects for the Hall Effect sensor based on a comparison of an aspect of the output based on the pseudorandom wideband calibration signal and the desired device response signal,
    provide a detected output comprising aspects of the output not based on the pseudorandom wideband calibration signal.

13. The apparatus of claim 12 wherein the processing circuit further comprises:
a calibration signal cancellation circuit configured to receive the output and the pseudorandom wideband calibration signal and provide a clean output signal removing effects of application of the pseudorandom wideband calibration signal to the Hall Effect sensor;
a decoder circuit configured to receive the output and the pseudorandom wideband calibration signal and provide the aspect of the output based on the pseudorandom wideband calibration signal for comparison to the desired device response signal.

14. The apparatus of claim 13 wherein the processing circuit further comprises:
a switched capacitor integrator circuit configured to receive the output and a clock signal for the pseudorandom wideband calibration signal;

a sample and hold circuit configured to receive output from the switched capacitor integrator circuit and the pseudorandom wideband calibration signal and provide the aspect of the output based on the pseudorandom wideband calibration signal for comparison to the desired device response signal.

\* \* \* \* \*